United States Patent [19]

Jang

[11] Patent Number: 5,342,297
[45] Date of Patent: Aug. 30, 1994

[54] BAILOUT RECEPTACLE FOR ANGIOPLASTY CATHETER

[76] Inventor: G. David Jang, 636 Golden West Dr., Redlands, Calif. 92373

[21] Appl. No.: 911,779

[22] Filed: Jul. 10, 1992

[51] Int. Cl.⁵ .............................. A61M 31/00
[52] U.S. Cl. ............................. 604/53; 604/96; 604/102; 604/280; 606/194
[58] Field of Search ............. 604/96, 101, 102, 264, 604/280, 49.52–49.53; 606/192–194; 128/656–658

[56] References Cited

U.S. PATENT DOCUMENTS

| | | |
|---|---|---|
| Re. 31,855 | 3/1985 | Osborne . |
| 3,297,030 | 1/1967 | Czorny et al. . |
| 3,550,591 | 12/1970 | MacGregor . |
| 3,682,173 | 8/1972 | Center . |
| 3,853,130 | 12/1974 | Sheridan . |
| 4,054,136 | 10/1977 | von Seppelin . |
| 4,079,738 | 3/1978 | Dunn et al. . |
| 4,175,564 | 11/1979 | Kwak . |
| 4,411,055 | 10/1983 | Simpson . |
| 4,411,654 | 10/1983 | Boarini et al. . |
| 4,464,176 | 8/1984 | Wijayarathna ............ 604/164 |
| 4,569,347 | 2/1986 | Frisbie . |
| 4,573,470 | 3/1986 | Samson et al. . |
| 4,581,017 | 4/1986 | Sahota . |
| 4,582,181 | 4/1986 | Samson ............... 606/194 |
| 4,585,013 | 4/1986 | Harris . |
| 4,619,644 | 10/1986 | Scott . |
| 4,631,056 | 12/1986 | Dye . |
| 4,631,059 | 12/1986 | Wolvek . |
| 4,705,507 | 11/1987 | Boyles . |
| 4,738,666 | 4/1988 | Fuqua . |
| 4,747,833 | 5/1988 | Kousai et al. . |
| 4,748,982 | 6/1988 | Horzewski et al. . |
| 4,762,129 | 8/1988 | Bonzel . |
| 4,771,777 | 9/1988 | Horzewski et al. .......... 604/101 X |
| 4,781,682 | 11/1988 | Patel ..................... 604/96 |
| 4,813,930 | 3/1989 | Elliott . |
| 4,888,000 | 12/1989 | McQuilken et al. . |
| 4,944,745 | 7/1990 | Sogard et al. . |
| 4,947,864 | 8/1990 | Shockey et al. . |
| 4,988,356 | 1/1991 | Crittenden et al. . |
| 4,997,424 | 3/1991 | Little . |
| 5,035,686 | 7/1991 | Crittenden et al. . |
| 5,040,548 | 8/1991 | Yock ..................... 128/898 |
| 5,046,503 | 9/1991 | Schneiderman . |
| 5,061,273 | 10/1991 | Yock . |
| 5,092,839 | 3/1992 | Kipperman ............. 604/53 |
| 5,102,403 | 4/1992 | Alt . |
| 5,135,535 | 8/1992 | Kramer . |
| 5,147,377 | 9/1992 | Sahota ................. 606/194 |
| 5,156,594 | 10/1992 | Keith .................... 604/96 |

FOREIGN PATENT DOCUMENTS 8203558  10/1982  PCT Int'l Appl. .

*Primary Examiner*—C. Fred Rosenbaum
*Assistant Examiner*—Corrine Maglione
*Attorney, Agent, or Firm*—Knobbe, Martens, Olson & Bear

[57] ABSTRACT

A bailout system for procedures involving angioplasty catheters, comprising a receptacle sized to fit inside an angioplasty guiding catheter, comprising an elongate tubular shaft having a lumen extending longitudinally therethrough from a proximal end to a distal end, a balloon angioplasty catheter extending through the lumen, the angioplasty catheter and the receptacle each adapted to slide longitudinally with respect to each other, and a longitudinally movable guidewire extending through the lumen but outside of the angioplasty catheter. Also disclosed is a method for using the system.

31 Claims, 12 Drawing Sheets

BAILOUT RECEPTACLE FOR ANGIOPLASTY CATHETER

BACKGROUND OF THE INVENTION

The present invention relates to a system for permitting rapid removal and reinsertion of angioplasty catheters, and is particularly useful in connection with fixed wire coronary balloon angioplasty catheters.

Percutaneous transluminal coronary angioplasty (PTCA) has gained widespread acceptance as a significantly less-invasive alternative to coronary bypass surgery. A similar technique, peripheral angioplasty, is useful in treatment of peripheral vascular disease. Unlike bypass surgery, PTCA does not require general anesthesia, cutting of the chest wall, extracorporeal profusion, or transfusion of blood.

During PTCA and other balloon angioplasty procedures, a catheter bearing an angioplasty balloon at the distal end is threaded into a stenosis (restriction of the artery) under fluoroscopic observation. Contrast agent is injected during the positioning process in order to permit real time imaging of the vasculature into which the catheter is inserted.

Once the catheter is in place in the stenosis, the angioplasty balloon is inflated, dilating the stenosis.

It is important that the inflated diameter of the balloon be matched to the native diameter of the stenotic vessel. A balloon that is too small will produce suboptimal dilation, while a balloon that is too large could result in arterial wall damage. Physicians tend to err on the side of choosing smaller (rather than larger) angioplasty balloons.

There are numerous occasions in which removal of the angioplasty catheter and reinsertion of another catheter may be required during PTCA. For example, coronary occlusion may occur during angioplasty. Dilation of one vessel may result in restriction of another, adjacent stenotic vessel. Furthermore, dissection of the arterial wall may occur during angioplasty. In both of these events, placement of a perfusion catheter through the stenotic region may be of utmost importance.

Furthermore, if the balloon chosen by the physician turns out to be a less than optimal size, removal of the angioplasty catheter and reinsertion of a different angioplasty catheter may be necessary.

One type of angioplasty catheter in widespread use is the over the wire catheter. This catheter has a guidewire lumen through which a steerable guidewire may be advanced. The guidewire (which extends distally beyond the distal end of the angioplasty catheter) is typically first positioned in the stenosis. Next, the catheter is advanced over the guidewire into the stenosis. If catheter exchange is necessary, the catheter may be removed from the patient leaving the guidewire in place, and a new catheter may be rapidly advanced over the positioned guidewire into the stenosis.

Another type of angioplasty catheter in widespread use is the fixed wire catheter. In this catheter, the distal end of the angioplasty balloon is actually bonded to the guidewire. Thus, the guidewire is "fixed" with respect to the location of the balloon. A major advantage of the fixed wire catheter is the elimination of the guidewire lumen extending through the balloon, permitting the deflated fixed wire balloons to have an extremely low profile. However, a significant disadvantage of the fixed wire catheter is the inability to rapidly remove the catheter and reinsert a different catheter into the same vasculature location. When the fixed wire catheter is removed, the guidewire is removed at the same time. Insertion of a new catheter is somewhat time consuming, requiring additional injection of contrast material and fluoroscopic observation during positioning of the second catheter. In essence, replacing a catheter with a second fixed-wire catheter is like starting the procedure all over again.

Accordingly, there is a substantial need for a system for bailing out fixed wire angioplasty catheters; that is, a system for permitting the removal of the fixed wire catheter and rapid and assured reinsertion of a second catheter into the same vascular location. Similarly, there is a need for a method for accomplishing that result.

SUMMARY OF THE INVENTION

In accordance with one embodiment of the invention, there is provided a bailout system for procedures involving angioplasty catheters, comprising a receptacle sized to fit inside an angioplasty guiding catheter, comprising an elongate tubular shaft having a lumen extending longitudinally therethrough from a proximal end to a distal end, a fixed-wire balloon angioplasty catheter extending through the lumen, the angioplasty catheter and the receptacle each adapted to slide longitudinally with respect to each other, and a longitudinally movable guidewire extending through the lumen but outside of the angioplasty catheter. The system may further comprise a guiding catheter in which the receptacle, the angioplasty catheter, and the guidewire are contained. The angioplasty catheter may be a peripheral angioplasty catheter, or may be a fixed wire coronary balloon angioplasty catheter. In one preferred system, the diameter of the receptacle shaft is 3.9 French or smaller. The receptacle may advantageously include an enlarged connector at the proximal end thereof through which the angioplasty catheter extends into the lumen. The receptacle may also include a side port extending through the shaft and adapted to receive a guidewire extending therethrough. The side port is preferably located toward the proximal end of the receptacle at a point ordinarily outside a patient during use of the system.

In one particularly preferred embodiment, the receptacle further includes a guidewire removing means for permitting removal of the guidewire laterally through the shaft, the guidewire removing means extending longitudinally along at least a portion of the shaft. The simplest guidewire removing means comprises a slit. Alternatively, the guidewire removing means is adapted to form a slit when lateral removal of the guidewire is desired. The guidewire removing means preferably extends distally along the shaft to within about 40 cm of the distal end of the receptacle. more preferably to within about 30, 25, 20, 15, or 10 cm. In one embodiment, the guidewire removing means extends distally along the shaft all the way to the distal end of the receptacle. When a system includes both a side port and a guidewire removing means, the guidewire removing means preferably extends distally from the side port.

The shaft of the receptacle advantageously has a first proximal segment and a second distal segment, wherein the first segment is more rigid than the second segment. The first segment may be made of a different material than the second segment. The second segment is preferably between about 1 and about 20 cm in length.

The present invention further includes a bailout system for procedures involving fixed-wire balloon angioplasty catheters, comprising a receptacle comprising an elongate tubular shaft having a lumen extending longitudinally therethrough from a proximal end to a distal end, and a fixed-wire balloon angioplasty catheter extending through the lumen, the angioplasty catheter and the receptacle each adapted to slide longitudinally with respect to each other, wherein the balloon angioplasty catheter has an angioplasty balloon having a maximum inflated diameter, and wherein the diameter of the lumen in the receptacle is not greater than the maximum inflated diameter of the balloon. This system also includes a guidewire extending through the lumen of the receptacle, and may be contained inside a guiding catheter in a patient.

The methods of the invention include a method for practicing balloon angioplasty, comprising the steps of: (a) positioning a bailout system according to the invention in a patient, so that a deflated angioplasty balloon of the angioplasty catheter is positioned in a stenosis, (b) inflating the balloon to dilate the stenosis, (c) advancing a bailout guidewire through the bailout receptacle and through the lesion, and (d) withdrawing the angioplasty catheter from the patient, leaving the bailout guidewire in the dilated lesion. In various embodiments, step (b) is performed before step (c); step (c) is performed before step (b); or step (c) is performed before step (a). One method further includes the step between steps (b) and (c) of advancing the distal end of the bailout receptacle through the stenosis. These methods may advantageously utilize a catheter having a guidewire removing means and may further comprise the final step of removing the receptacle from the patient while maintaining the position of the distal end of the bailout guidewire in the lesion, so that the bailout guidewire is rapidly removed laterally from the receptacle through the guidewire removing means.

Finally, the invention includes a method for dilating a bifurcation double lesion, comprising the ordered steps of: (a) advancing a system according to the present invention into the right or left coronary artery of a human patient having coronary bifurcation lesion disease at a branch of the artery, so that the angioplasty balloon is in a first bifurcation lesion, and advancing a bailout guidewire through the bailout receptacle so that the bailout guidewire is extending through a second bifurcation lesion, (b) inflating the balloon to dilate the first bifurcation lesion, (c) reversing the respective positions of the balloon and the bailout guidewire, so that the bailout guidewire is in the dilated first bifurcation lesion and the balloon is in the second bifurcation lesion, and (d) inflating the balloon to dilate the second bifurcation lesion.

DETAILED DESCRIPTION OF THE INVENTION

In the present invention, there is provided a coaxial bailout system comprising a relatively small receptacle in the form of a hollow catheter with the fixed wire balloon catheter inside of the receptacle. Unlike the relatively large guiding catheter used in angioplasty procedures, the receptacle of the present invention has a diameter much closer to the diameter of a balloon angioplasty catheter. The fixed-wire angioplasty catheter (or other catheter) extending through the bailout receptacle may slide longitudinally in the distal and proximal directions through the receptacle.

Figure 1:
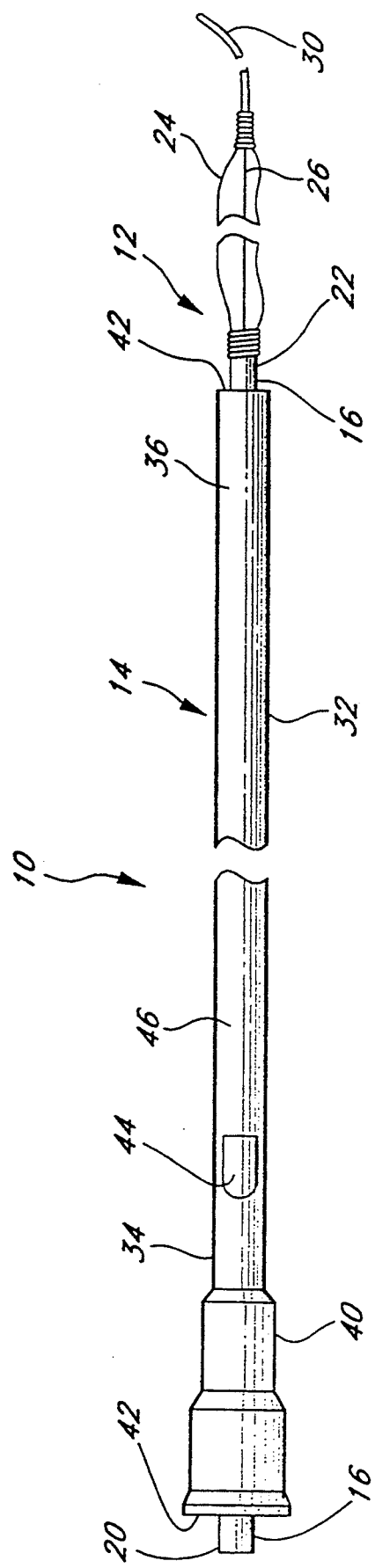
FIG. 1 is a side elevation of the system of the present invention, comprising a bailout receptacle with a fixed-wire balloon angioplasty catheter extending therethrough.

With reference now to FIG. 1, the bailout system 10 of the present invention comprises an angioplasty catheter 12 extending through a bailout receptacle 14. The angioplasty catheter 12 may be a catheter of any suitable design for performing coronary angioplasty or peripheral angioplasty. However, the angioplasty catheter 12 is preferably a fixed wire balloon angioplasty catheter.

The angioplasty catheter 12 comprises a catheter shaft 16 having a proximal end 20 and a distal end 22. An inflatable/deflatable angioplasty balloon of conventional design is mounted on the distal end 22 of the catheter shaft 16. If the angioplasty catheter is a conventional fixed wire coronary angioplasty catheter, the balloon 24 has a proximal end attached to the distal end 22 of the catheter shaft 16. A fixed guidewire 26 extends through the balloon 24, and the distal end of the balloon 24 is attached securely to the fixed guidewire 26. The guidewire tip 30 may advantageously be a shapeable tip of conventional design.

The bailout receptacle 14 comprises a elongated cylindrical shaft 32 with a proximal end 34 and a distal end 36. A proximal fitting 40, preferably of molded plastic, is provided on the proximal end 34 of the receptacle 14. A lumen 42 extends through the receptacle 14 from the proximal end 34 to the distal end 36. The receptacle lumen 42 is sized only slightly larger than the diameter of the angioplasty catheter 12, and is sized so that the angioplasty catheter 12 can slide proximally and distally through the receptacle lumen 42.

In one preferred embodiment, the diameter of the receptacle shaft 32 is 3.9 French or smaller (e.g., in the case of a bailout system for coronary use). The receptacle shaft will be larger for peripheral angioplasty.

In one preferred embodiment of the system 10, a proximal side port 44 is provided, extending through the wall 46 of the receptacle shaft 32. The proximal side port 44 is sized to permit insertion and removal of a distally-extending movable guidewire (not shown in FIG. 1).

Figure 2:
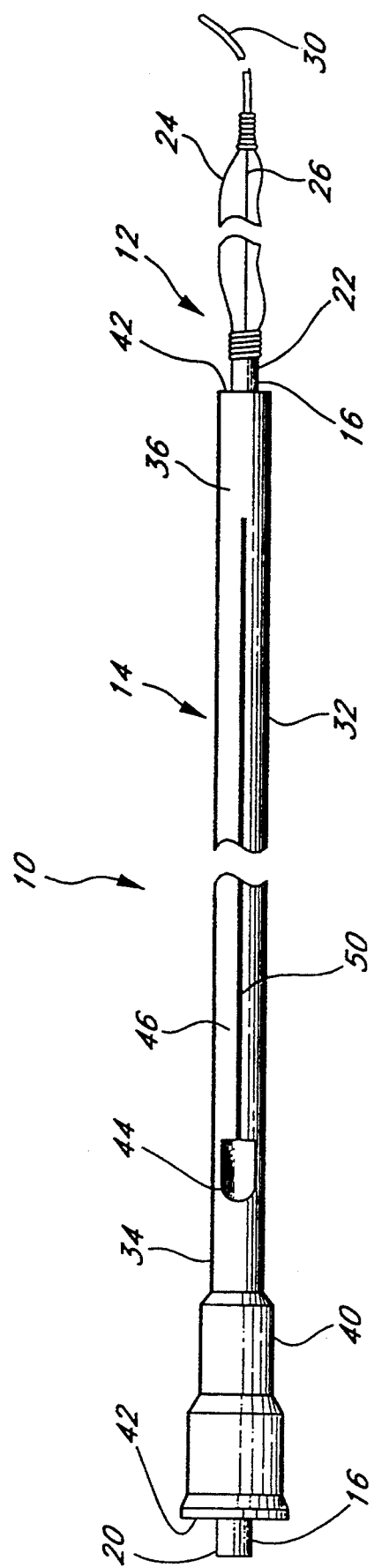
FIG. 2 corresponds to FIG. 1, but further illustrates a guidewire removing means for removing a guidewire laterally through the wall of the receptacle.

In a preferred embodiment, as illustrated in FIG. 2, the wall 46 of the receptacle shaft 32 is provided with a guidewire removing means 50 extending distally from the general vicinity of the proximal end 34 of the receptacle shaft 32. In the embodiment illustrated in FIG. 2, the guidewire removing means 50 extends distally from the proximal side port 44. The guidewire removing means 50 can extend distally any desired distance; however, in a preferred embodiment, the guidewire removing means 50 extends distally to within about 40 cm of the distal end 36 of the receptacle 14; preferably to within about 30, 25, or 20 cm, and more preferably to within about 10 or 5 cm of the distal end 36 of the receptacle 14. In one preferred embodiment, the guidewire removing means 50 extends all the way to the distal end 36 of the receptacle 14.

The guidewire removing means illustrated in FIG. 2 comprises a simple slit. It will be understood, however, that the guidewire removing means 50 may comprise any other type of structure that will permit removal of a guidewire laterally through the wall 46 of the receptacle 14. Thus, for example, the guidewire removing means 50 may comprise not only a fully formed slit, but an inchoate slit (e.g., a weakened area that readily may be ruptured or slit to permit lateral removal of the guidewire). Alternatively, the guidewire removing means may comprise an interrupted or perforated slit, a tear-away strip, parallel weakened lines or parallel interrupted slits to permit removal of a strip, and other similar structures.

In a preferred embodiment, the bailout receptacle 14 (like the angioplasty catheter 12) is formed of molded or extruded polymer material. Without intending to limit the invention, polymer materials having suitable characteristics may be selected from polyethylene, polypropylene, polyvinyl chloride, polyvinylidene chloride, polyethylene terephthalate, polysiloxane, and other well known polymer materials.

Figure 3:
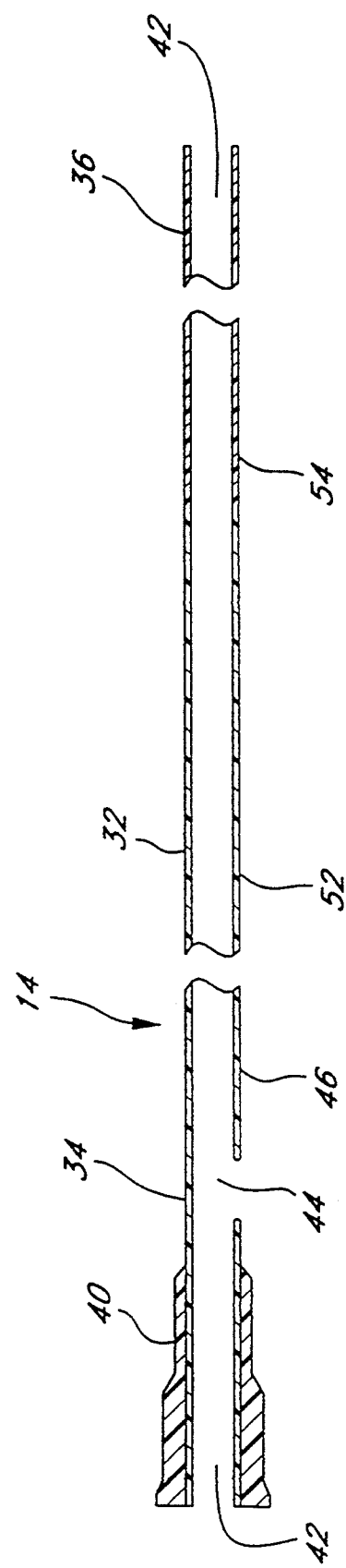
FIG. 3 is a longitudinal cross section of the receptacle of FIG. 1.

FIG. 3 illustrates a longitudinal cross section of one preferred embodiment of the bailout receptacle 14 of the present invention. As illustrated in FIG. 3, the bailout receptacle 14 has a fitting 40 molded to or otherwise attached to the proximal end 34 of the receptacle shaft 32. The fitting 40 is preferably annular, and is advantageously formed of relatively rigid material to permit the physician to securely grip and hold the proximal end 34 of the receptacle 14 at the fitting 40. FIG. 3 more clearly illustrates the lumen 42 extending longitudinally from the proximal end 34 to the distal end 36 of the receptacle 14. The wall 46 of the receptacle 14 has a proximal side port 44 formed therein, permitting access from a point normally outside the patient through the outside wall 46 of the receptacle 14 into the lumen 42 of the receptacle 14.

In the embodiment illustrated in FIG. 3, the receptacle shaft 32 includes a proximal segment 52 and a distal segment 54. The proximal segment 52 and the distal segment 54 may advantageously be made of different materials. Specifically, it is advantageous to form the proximal segment 52 of a more rigid material, and to form the distal segment 54 of a more pliable material. Alternatively, the wall thicknesses of the receptacle shaft 32 may be adjusted so that the distal segment 54 is more pliable or flexible than the proximal segment 52.

One advantage of having a 2-segment receptacle 14 is that the stiffer proximal segment can provide pushability, whereas the distal segment is sufficiently pliable to easily permit negotiation of coronary arteries without undo rigidity and without causing damage to the arteries. In practice, the distal segment may advantageously comprise the portion of the receptacle 14 extending distally from the guiding catheter (not shown in FIG. 3) and may, therefore, be between about 1 cm and 20 cm in length, preferably between about 3 cm and about 10 or 15 cm in length.

Figure 4:
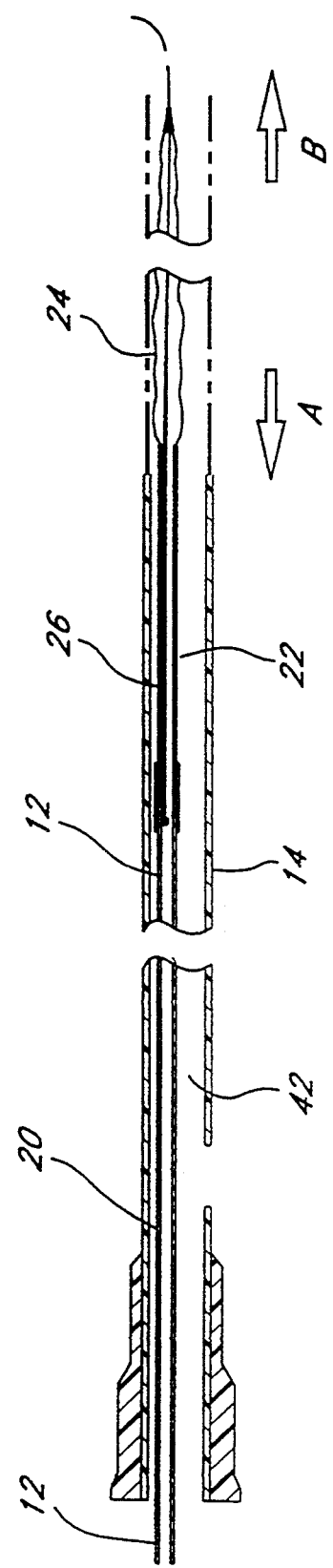
FIG. 4 is a longitudinal cross section of the system of FIG. 1, illustrating both the angioplasty catheter and the bailout receptacle in longitudinal cross section.

FIG. 4 is another longitudinal section of the receptacle 14, this time also showing the angioplasty catheter 12 in cross section inside the receptacle 14.

In FIG. 4, the angioplasty catheter 12 is a composite catheter, in which the proximal end 20 of the catheter shaft is formed of a rigid material (such as stainless steel hypotube), and the distal end 22 of the catheter shaft is formed of a more flexible material, such as extruded polymer. The fixed guidewire 26 in FIG. 4 is bonded to the proximal hypotube end 20 of the catheter shaft, and extends distally from the hypotube through the balloon 24.

FIG. 4 illustrates that, deflated, the balloon 24 is sized to fit easily within the receptacle lumen 42 in sliding engagement therewith. The proximal-pointing arrow A and the distal-pointing arrow B indicate that the receptacle 14 may be advanced distally (in the direction of arrow B) over the balloon 24, as illustrated in phantom, or alternatively that the balloon 24 may be withdrawn inside the receptacle 14. Similarly, the receptacle 14 may be moved proximally in the direction of arrow A with respect to the angioplasty catheter 12.

Figure 5:
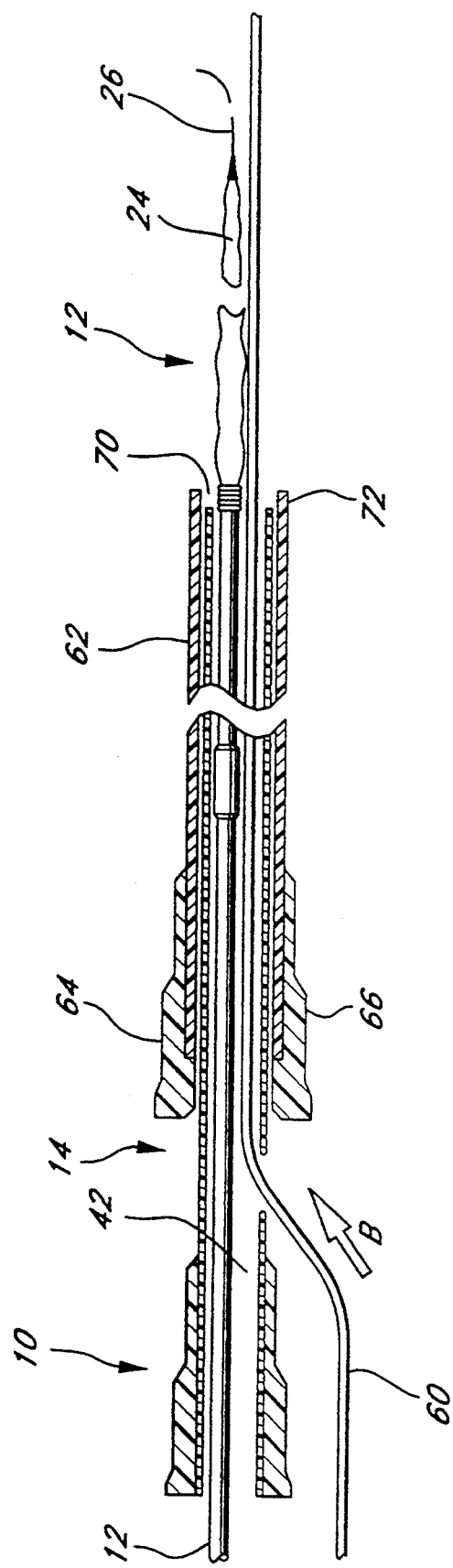
FIG. 5 is a longitudinal cross section of the bailout system of the present invention with a bailout guidewire extending through the receptacle along side the angioplasty catheter, with the entire system being positioned inside a guiding catheter.

In one particularly preferred embodiment of the invention, the bailout system 10 includes a bailout guidewire 60 inserted into the lumen 42 of the receptacle 14. FIG. 5 illustrates the bailout system 10 of the present invention in place in a guiding catheter 62 of conventional design. The guiding catheter 62 includes a proximal fitting 64 at the proximal end 66 of the guiding catheter, and a distal opening 70 at the distal end 72 of the guiding catheter 62.

With the bailout system 10 of the present invention in place in a patient, the angioplasty catheter 12 extending through the bailout receptacle 14, and the bailout receptacle 14 extending distally into the guiding catheter 62, one may desire to advance a bailout guidewire 60 distally inside the bailout receptacle 14. In this embodiment, the receptacle lumen 42 of the receptacle 14 is of sufficient size to permit proximal and distal sliding motion of the bailout guidewire 60 and the angioplasty catheter 12 with respect to the bailout receptacle 14, while at the same time the bailout receptacle 14 is sufficiently small (e.g., 3.9 French or smaller for coronary use) to fit easily within a conventional guiding catheter.

As illustrated in FIG. 5, when the balloon 24 of the angioplasty catheter is extending distally from the distal opening 70 of the guiding catheter 62 (presumably having been positioned e.g., within a coronary artery in a patient), the bailout guidewire 60 may be advanced distally alongside the balloon 24 and the fixed guidewire 26. The arrow B in FIG. 5 indicates distally directed motion of the bailout guidewire 60.

Figure 6:
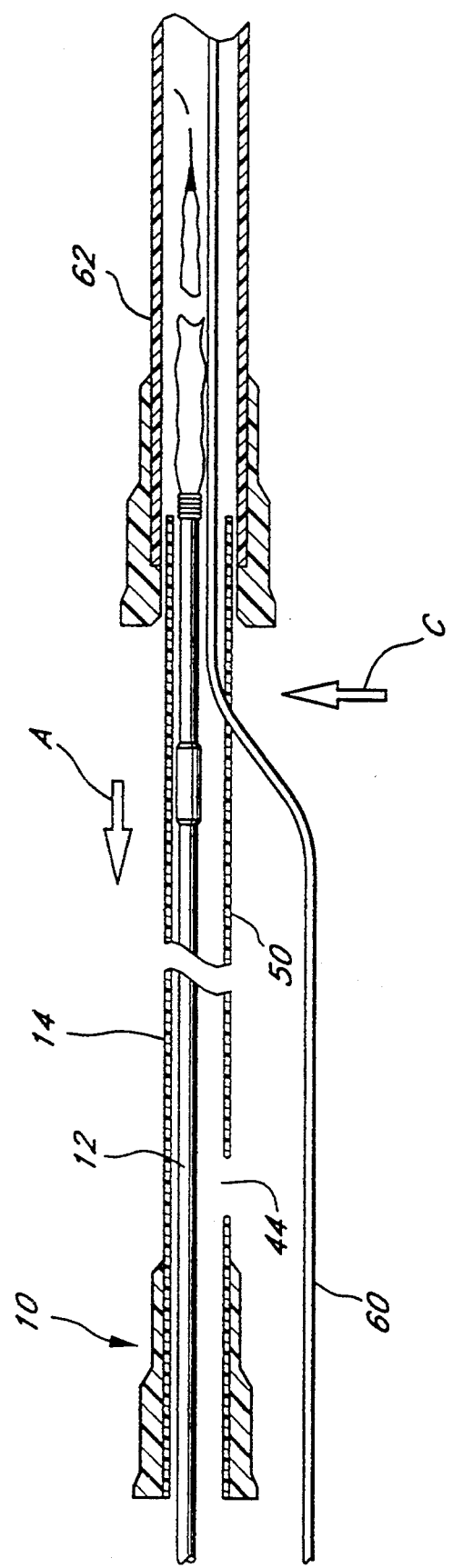
FIG. 6 corresponds to FIG. 5, and illustrates the proximal removal of the bailout receptacle and the angioplasty catheter while maintaining the bailout guidewire in place.

With the bailout system 10 of the present invention in place in a patient, the bailout receptacle 14 may be advanced over the angioplasty catheter 12 to a desired position, the angioplasty catheter 12 may be removed from the patient, and a new catheter (such as a balloon angioplasty catheter) may be reinserted through the bailout receptacle 14 to the same position. Alternatively, if a bailout guidewire 60 has been inserted through the bailout receptacle 14 alongside the fixed wire angioplasty catheter 12, one may remove both the angioplasty catheter 12 and the bailout receptacle 14 from the patient while leaving the bailout guidewire 60 in place. FIG. 6 illustrates the removal of the angioplasty catheter 12 and the bailout receptacle 14 while maintaining a bailout guidewire 60 in place in the patient.

In the embodiment illustrated in FIG. 6, the bailout receptacle has a guidewire removing means 50 extending distally from the proximal sideport 44. As illustrated in FIG. 6, the bailout receptacle 14 and angioplasty catheter 12 are removed proximally in the direction of arrow A. Arrow C illustrates that the bailout guidewire 60 is maintained in a fixed position (and does not move proximally with the remainder of the system 10). By holding the bailout guidewire 60 stationary, the bailout guidewire 60 is passed laterally outward through the guidewire removing means 50.

Figure 7:
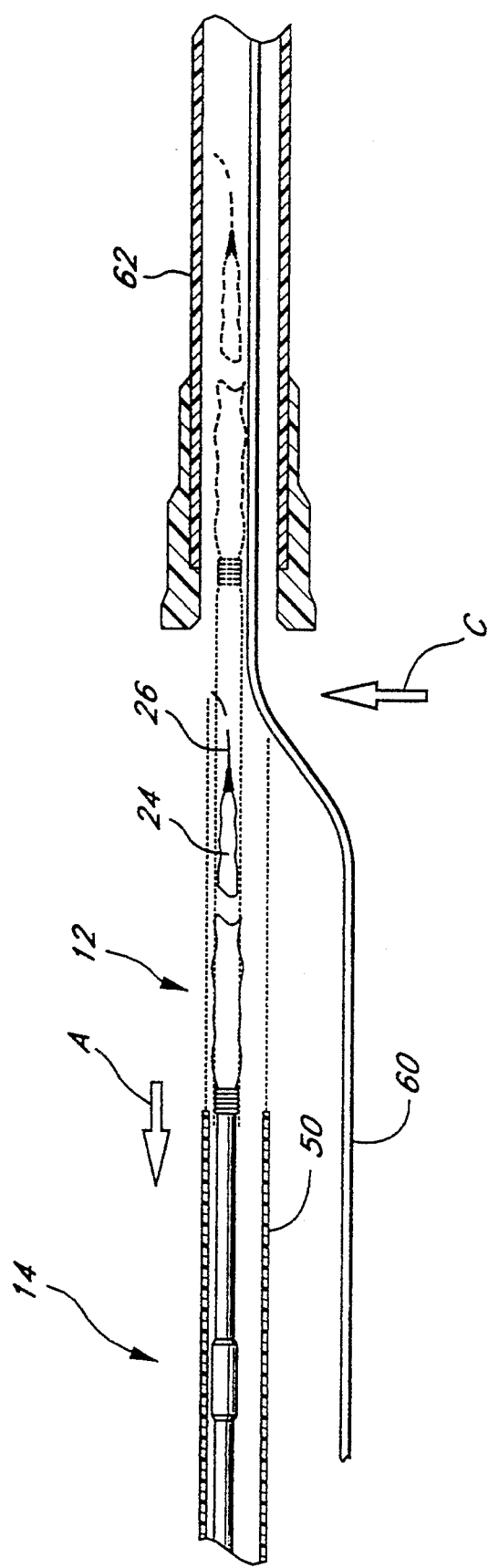
FIG. 7, corresponds to FIG. 6, except that the bailout system comprising the bailout receptacle and the angioplasty catheter have been completely removed from the guiding catheter and the bailout guidewire.
Figure 8A:
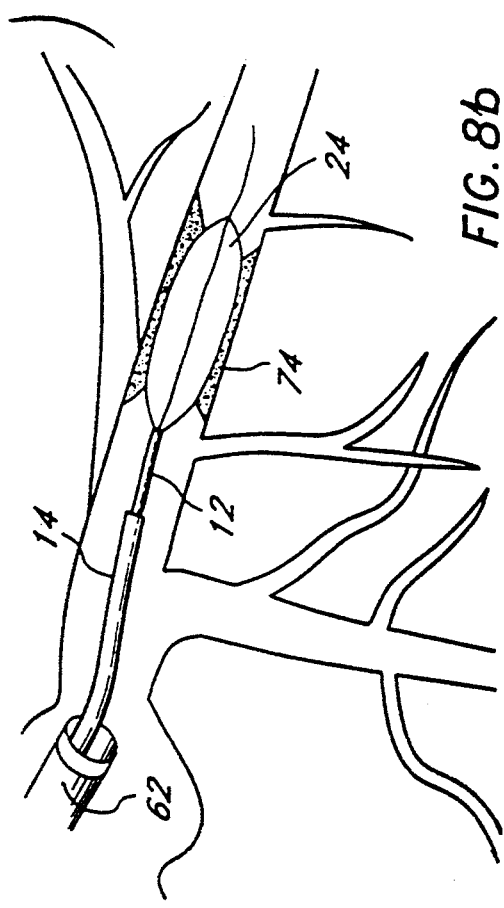
FIG. 8, Panels A-D, illustrate one method of the present invention.
Figure 8B:
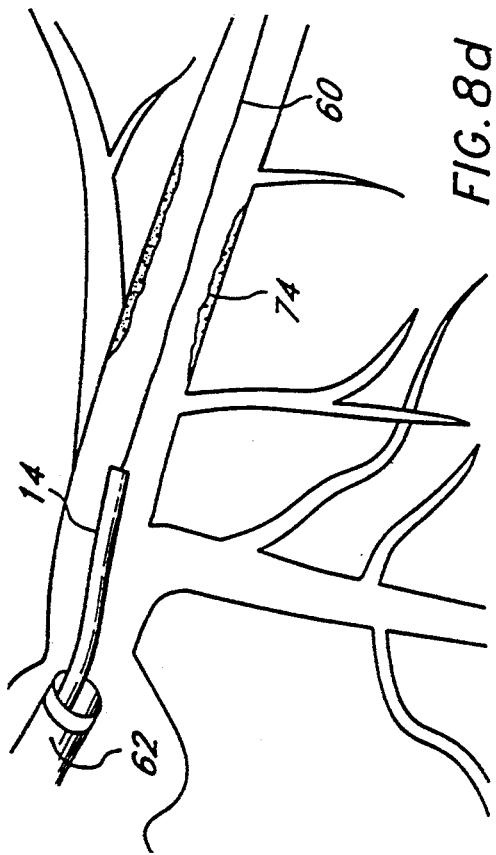
Figure 8C:
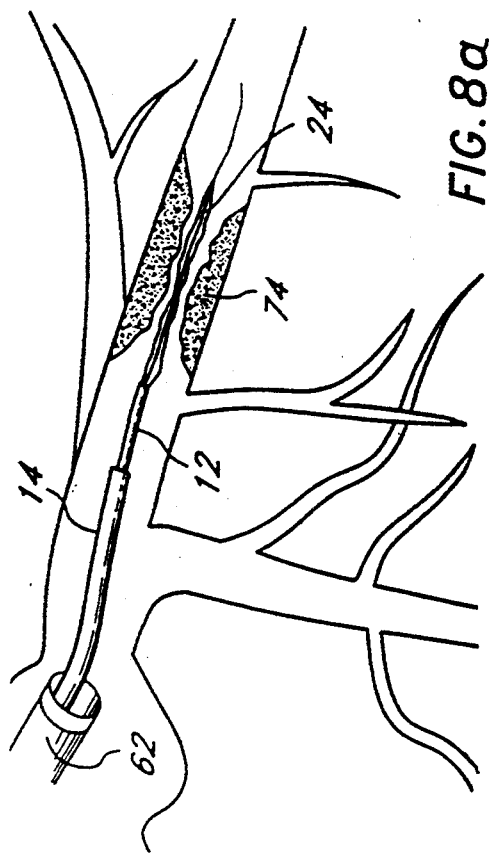
Figure 8D:
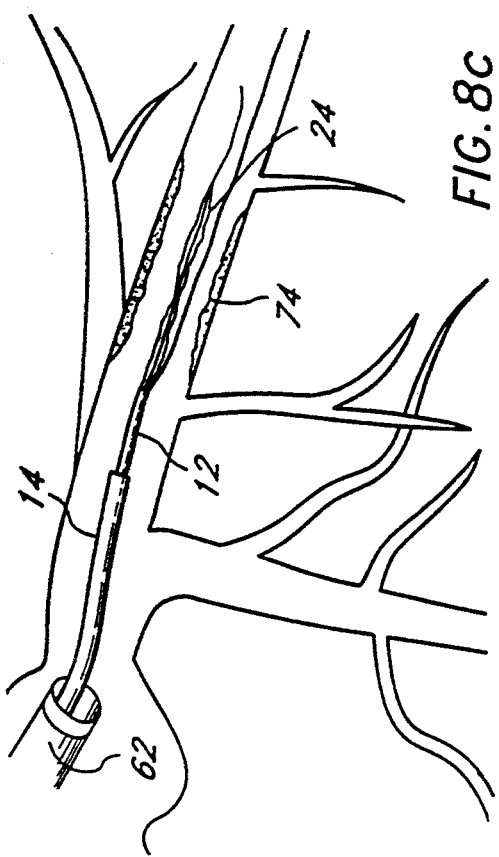
Figure 9A:
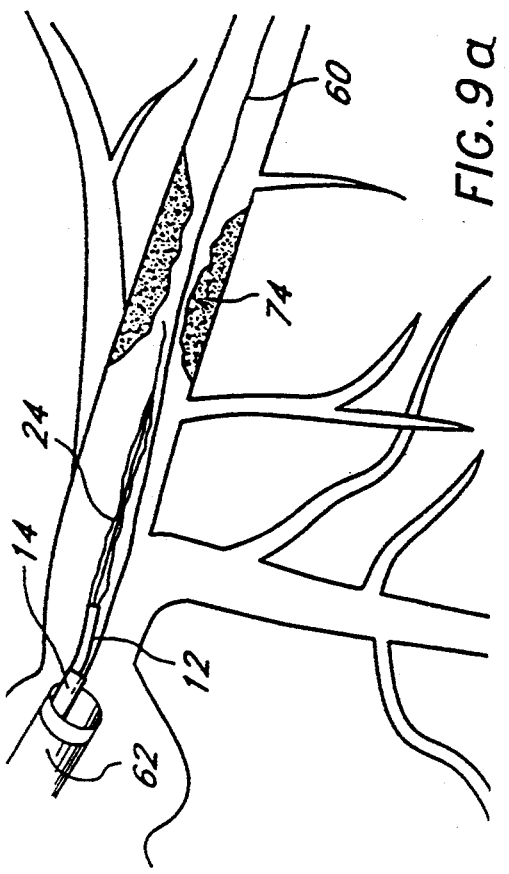
FIG. 9, Panels A-D, illustrate a second method for practicing the present invention.
Figure 9B:
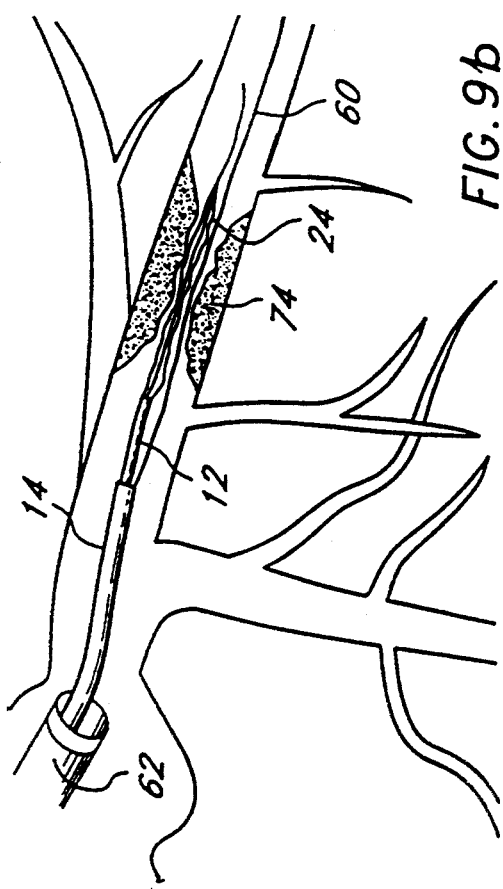
Figure 9C:
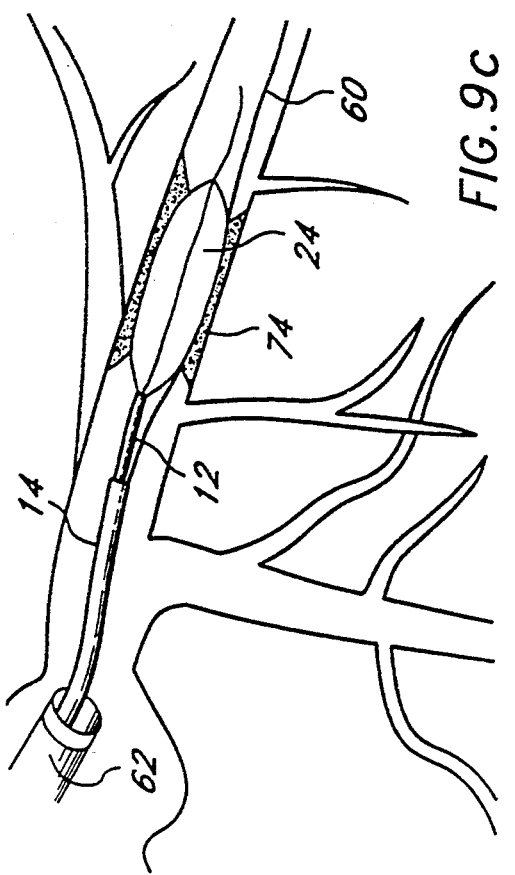
Figure 9D:
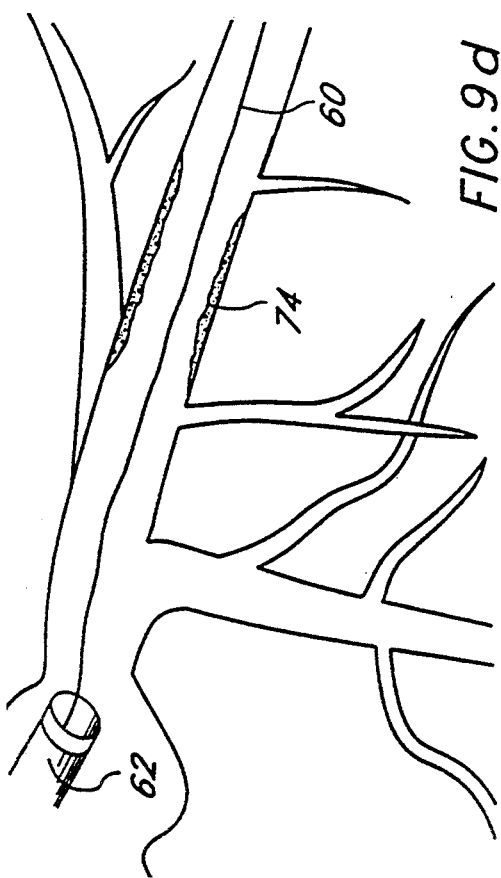
Figure 10B:
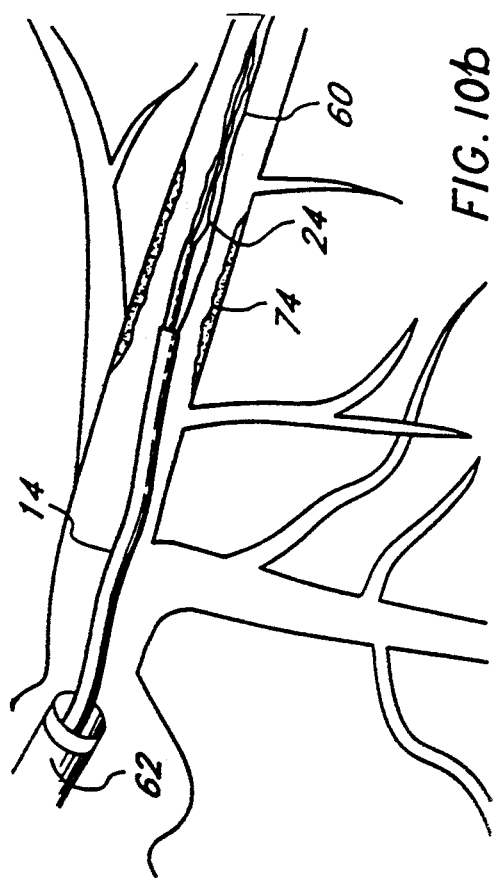
FIG. 10, Panels A-D, illustrate yet another method for practicing the present invention.
Figure 10D:
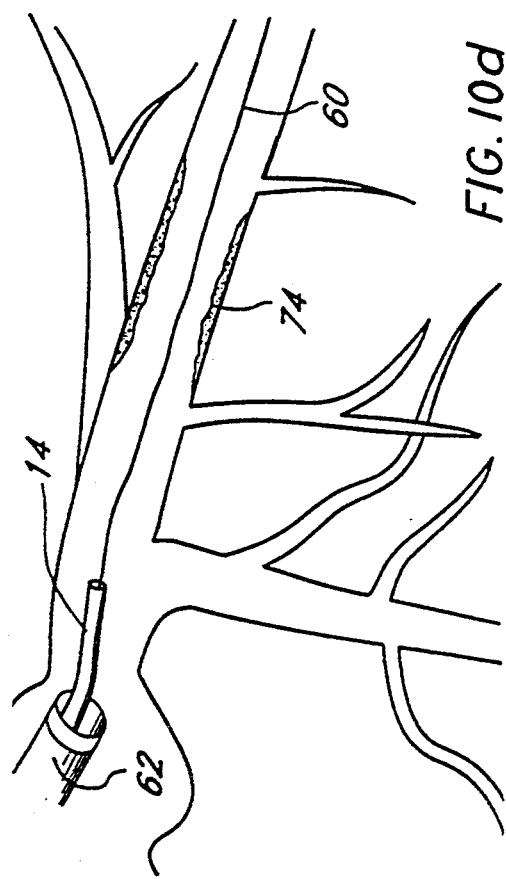
Figure 10A:
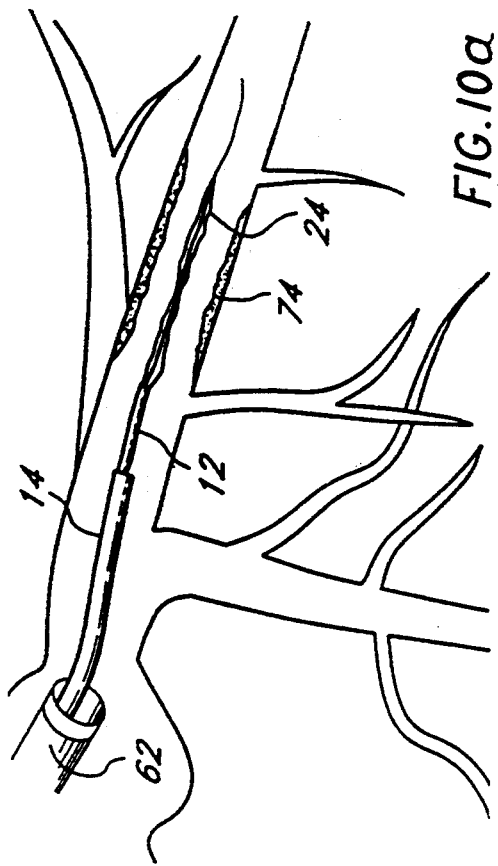
Figure 10C:
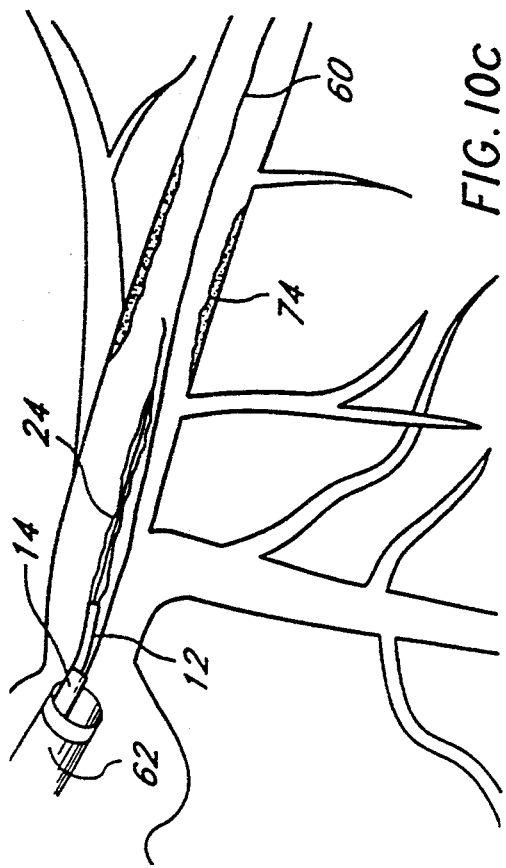
Figure 11A:
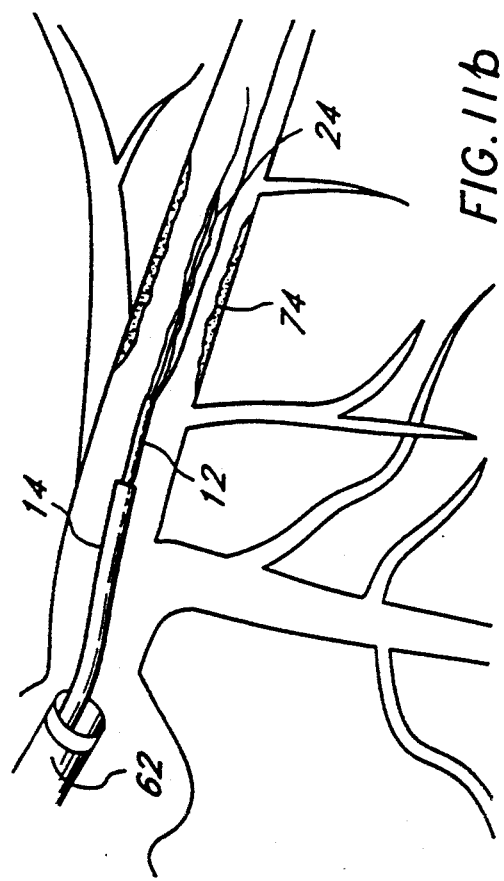
FIG. 11, Panels A-D, illustrate still another method for practicing the present invention.
Figure 11B:
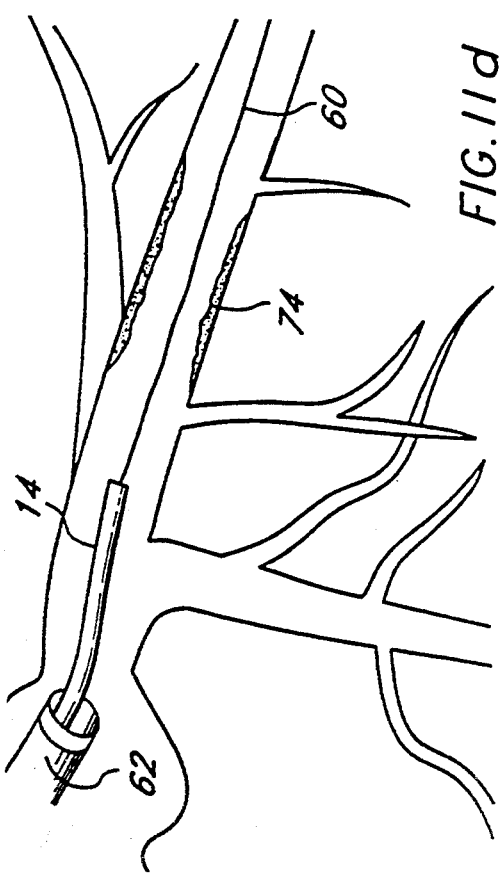
Figure 11C:
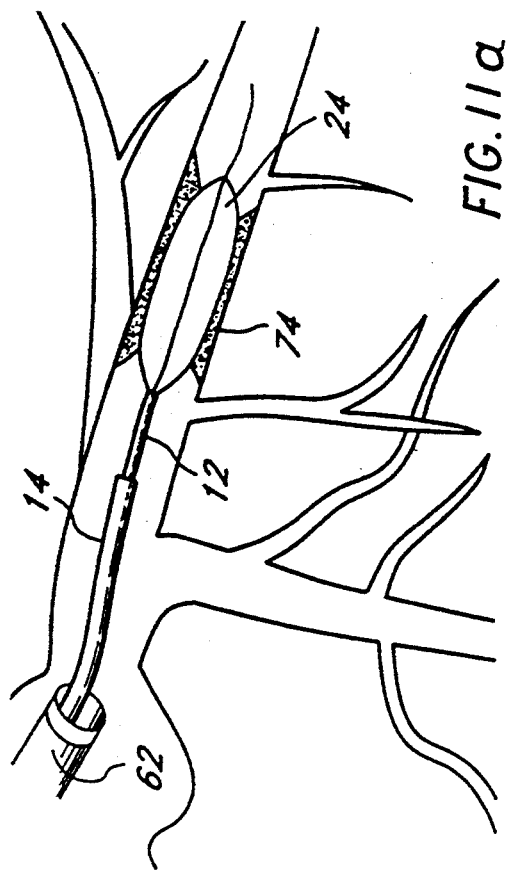
Figure 11D:
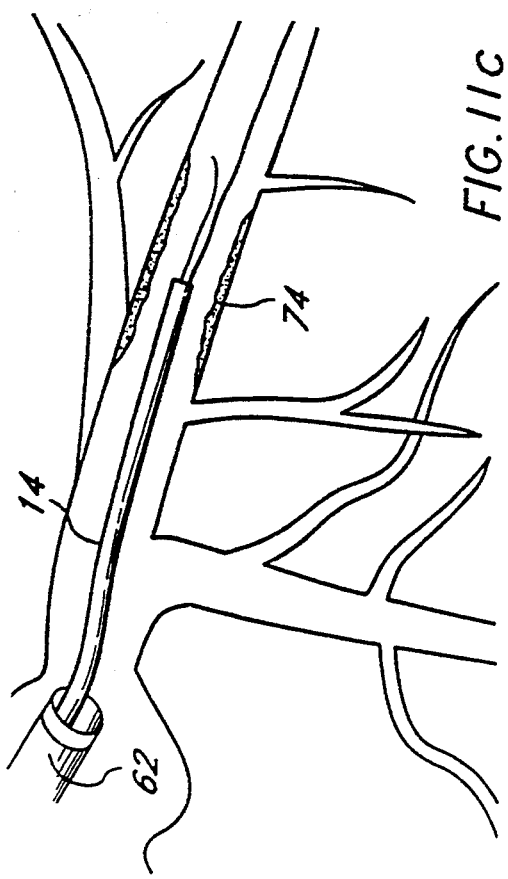
Figure 12A:
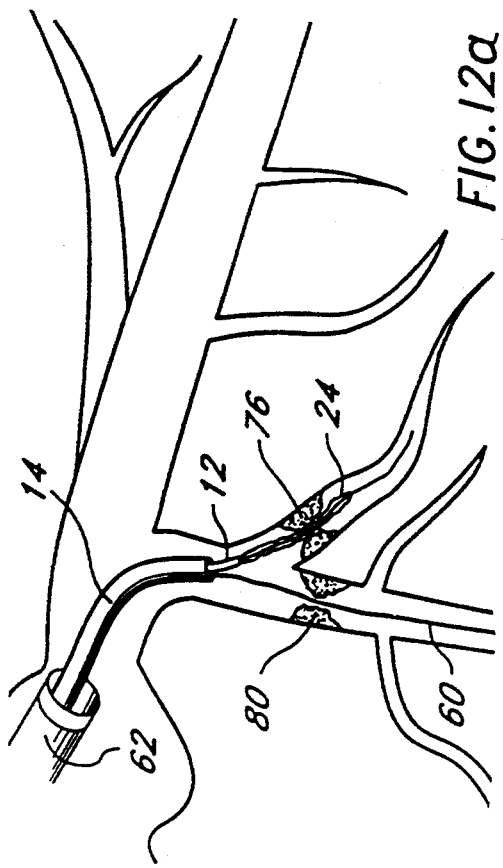
FIG. 12, Panels A-D, illustrate the method of the present invention in use in a bifurcation lesion in a patient.
Figure 12B:
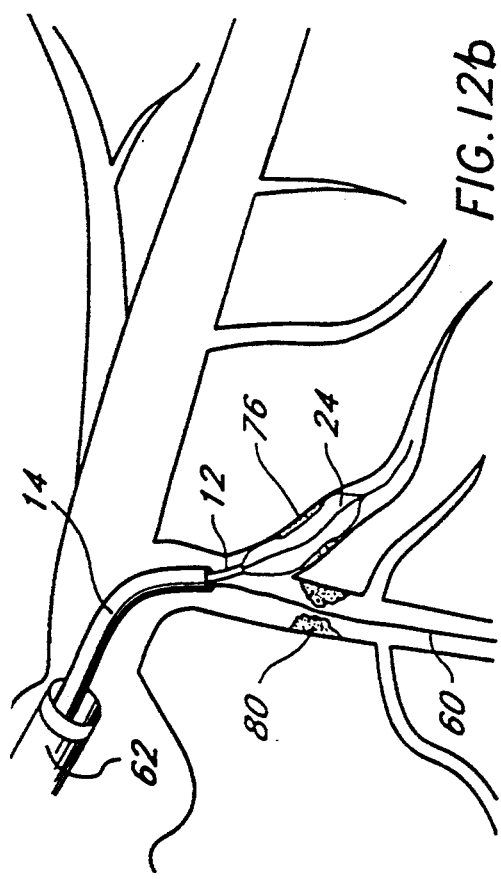
Figure 12C:
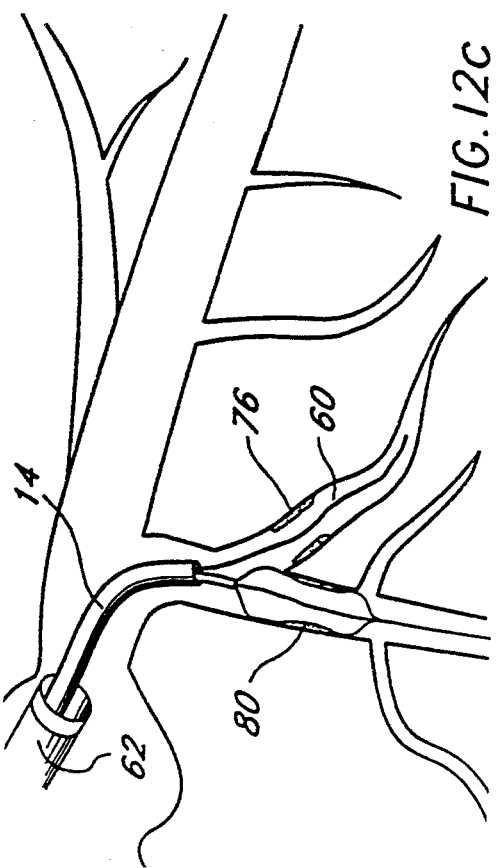
Figure 12D:
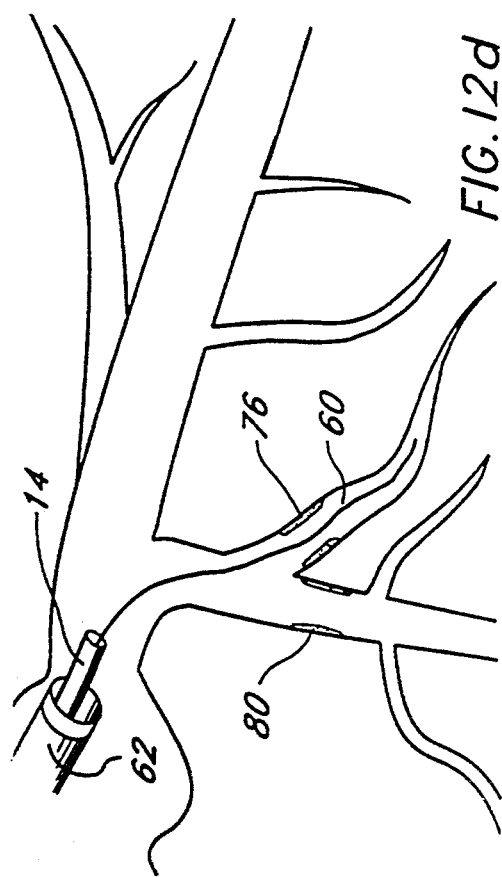

FIG. 7 illustrates the completion of the removal process, in which the angioplasty catheter 12 and the receptacle 14 continue to move proximally in the direction of arrow A, while the bailout guidewire 60 is held in a fixed position as illustrated by arrow C. The guidewire removing means 50 in FIG. 7 extends to the distal end of the bailout receptacle 14, so that the bailout receptacle 14 may be removed completely off of the bailout guidewire 60.

FIGS. 8-12 illustrate different methods for using the bailout system 10 of the present invention.

In the scenario illustrated in the four panels (A-D) of FIG. 8, the guiding catheter 62 extends through the aorta to the coronary artery system, with the bailout receptacle 14 extending distally from the guiding catheter 62. The deflated angioplasty catheter 12 extends distally from the bailout receptacle and is positioned so that the deflated angioplasty balloon 24 is positioned within an arterial lesion 74. In panel B, the angioplasty balloon 24 is inflated to dilate the stenosis or lesion 74. Panel C illustrates the bailout guidewire 60 being advanced from the distal end of the bailout receptacle 14, past the deflated balloon 24 and through the dilated lesion 74. The angioplasty balloon 24 in Panel C is deflated prior to advancing the bailout guidewire 60 past the balloon 24. In Panel D, the angioplasty catheter 12 has been withdrawn into the bailout receptacle 14 and may be removed from the patient, leaving the bailout guidewire 60 in place in the lesion 74 in the event another catheter should need to be positioned inside the lesion 74 rapidly and securely.

FIG. 9 is similar to FIG. 8, except that the bailout guidewire 60 is advanced through the lesion prior to insertion of the angioplasty balloon 24 in the lesion 74. Thus, in Panel A, the bailout guidewire crosses the lesion 74; in Panel B, the balloon 24 of the angioplasty balloon catheter 12 is positioned inside the lesion 74; in Panel C, the balloon 24 is inflated in the stenosis or lesion 74, with the bailout guidewire 60 also extending through the lesion 74 outside of the balloon 24; and in Panel D, the receptacle 14 and the catheter 12 have been removed, leaving the bailout guidewire 60 in place in the stenosis 74.

FIG. 10 illustrates yet another embodiment of the method of the present invention. In Panel A, the stenosis has already been dilated by the balloon 24, and the balloon 24 has been deflated. In Panel B, the angioplasty catheter 12 and the receptacle 14 are advanced as a unit through the dilated lesion 74, and then the bailout guidewire 60 is advanced through the bailout receptacle 14. Next, in Panel C, the receptacle 14 and the angioplasty catheter 12 are withdrawn proximally while the bailout guidewire 60 is maintained in its position within the lesion 74. Finally, in Panel D, the guidewire 60 is in place in the artery while the angioplasty catheter 12 (and, optionally, the bailout receptacle 14) have been removed proximally out of the patient. Another catheter may then be advanced over the guidewire 60 through the lesion.

In the scenario of FIG. 11, the fixed-wire balloon angioplasty catheter 12 is positioned with the angioplasty balloon 24 inside the stenosis 74 and the receptacle 14 extending to within close proximity of the balloon 24. The balloon 24 is then inflated in the stenosis 74 to dilate the stenosis 74. In Panel B, the balloon is deflated, and in Panel C, the receptacle 14 is advanced through the dilated lesion 74 and over the balloon of the angioplasty catheter 12. The bailout guidewire 60 is then advanced through the bailout receptacle 14, extending through the dilated lesion 74. The balloon catheter 12 and the bailout receptacle 14 are then withdrawn, as shown in Panel D, leaving the bailout guidewire 60 extending through the dilated lesion 74.

FIG. 12 illustrates use of the present invention in a bifurcation double lesion. In a patient suffering from bifurcation/double lesion coronary disease, the patient has lesions near the branching point of a coronary artery. The scenario of FIG. 12 is a particularly difficult scenario for balloon angioplasty, because dilation of a first lesion 76 may tend to close the second lesion 80, and vice versa. Thus, before attempting angioplasty on the double lesions 76, 80, the physician must provide a guidewire through the lesion not being dilated at that moment as a safety precaution.

With reference to Panel A in FIG. 12, the deflated balloon 24 is placed in the first lesion 76, with the bailout guidewire 60 positioned through the second lesion 80. Then, as shown in Panel B, the balloon 24 is inflated to dilate the first stenosis 76, with the bailout guidewire extending out of the distal end of the bailout receptacle 14 and through the second lesion 80.

The positions of the angioplasty balloon 24 and the bailout guidewire 60 are then switched, so that the bailout guidewire 60 extends through the dilated first lesion 76, and the angioplasty balloon is positioned in the second stenosis 80, as shown in Panel C. The balloon 24 is inflated to dilate the second stenosis. The angioplasty catheter 12 may then be withdrawn with the receptacle 14, leaving the bailout guidewire 60 in the first vessel extending through the first lesion 76.

It will be appreciated that the method of the invention may also be practiced without a bailout guidewire 60 by positioning the bailout receptacle 14 inside the dilated site (as illustrated in Panel B of FIG. 10). The angioplasty catheter 12 is then withdrawn from the patient and a new catheter may be inserted through the bailout receptacle 14 and through the lesion 74 of FIG. 10, Panel B.

Although the apparatus and method of the present invention have been described in the context of particular embodiments, it will be appreciated that the present invention may be practiced with catheters other than balloon angioplasty catheters. It will also be appreciated that the catheter reinserted into the patient utilizing the present invention may be any suitable type of catheter, including another balloon angioplasty catheter (either fixed wire or over-the-wire), an atherectomy catheter, a laser catheter, a perfusion catheter, other vascular catheter.

Furthermore, it will be appreciated that numerous modifications and variations of the preferred embodiments are possible, while remaining within the scope of the intended invention. Accordingly, the claims that follow are not to be limited to any particular disclosed embodiment, but instead should be entitled to their full literal scope, together with reasonable equivalents.

What is claimed is:

1. A method for practicing balloon angioplasty, comprising the steps of:
   a. providing a bailout system, said bailout system comprising:
      a receptacle comprising an elongate tubular shaft having a lumen of a substantially constant diameter extending longitudinally therethrough from a proximal end to a distal end, said receptacle being adapted to extend longitudinally through a guiding catheter; and
      a balloon angioplasty catheter having a proximal end and a distal end and an angioplasty balloon at or near the distal end of the catheter, said balloon in communication with a balloon inflation lumen and said balloon further having a maximum inflated diameter, said angioplasty catheter extending through said lumen, said angioplasty catheter and said receptacle each adapted to freely slide longitudinally with respect to each other, and wherein the diameter of the lumen in the receptacle is not greater than the maximum inflated diameter of the balloon;
   b. positioning the bailout system in a patient, so that the angioplasty balloon of the angioplasty catheter is positioned in a stenosis;
   c. inflating and deflating the balloon to dilate the stenosis;
   d. advancing the distal end of the bailout receptacle through the stenosis;
   e. then advancing a guidewire through the bailout receptacle and through the lesion, such that the guidewire is outside of said catheter along the entire length of said catheter; and
   f. withdrawing the angioplasty catheter from the patient, leaving the guidewire in the dilated lesion.

2. The method of claim 1, wherein said receptacle further comprises guidewire removing means for permitting removal of a guidewire laterally through the shaft, said guidewire removing means extending longitudinally along at least a portion of the shaft, further comprising the final step of removing the receptacle from the patient while maintaining the position of the bailout guidewire in the lesion, so that the bailout guidewire is removed laterally from the receptacle through the guidewire removing means.

3. A method for dilating a bifurcation double lesion, comprising the ordered steps of:
   (a) providing a bailout system, said bailout system comprising:
      a receptacle comprising an elongate tubular shaft having a lumen of a substantially constant diameter extending longitudinally therethrough from a proximal end to a distal end, said receptacle being adapted to extend longitudinally through a guiding catheter; and
      a balloon angioplasty catheter having a proximal end and a distal end and an angioplasty balloon at or near the distal end of the catheter, said balloon in communication with a balloon inflation lumen and said balloon further having a maximum inflated diameter, said angioplasty catheter extending through said lumen, said angioplasty catheter and said receptacle each adapted to freely slide longitudinally with respect to each other, and wherein the diameter of the lumen in the receptacle is not greater than the maximum inflated diameter of the balloon;
   (b) advancing the system into the coronary artery of a human patient having coronary bifurcation lesion disease at a branch of said artery, so that the angioplasty balloon is in a first bifurcation lesion, and advancing a guidewire through said bailout receptacle so that the guidewire is extending through a second bifurcation lesion, such that the guidewire is outside of said catheter along the entire length of said catheter;
   (c) inflating and deflating the balloon to dilate the first bifurcation lesion;
   (d) reversing the respective positions of the balloon and the bailout guidewire, so that the guidewire is in the dilated first bifurcation lesion and the balloon is in the second bifurcation lesion; and
   (e) inflating and deflating the balloon to dilate the second bifurcation lesion.

4. The method of claim 3, comprising, in addition to steps (a)-(d), the step of withdrawing the balloon catheter from the second dilated lesion, and allowing the guidewire to remain in one of the two dilated lesions for bailout purposes.

5. A bailout system for procedures involving angioplasty catheters, comprising:
   a guiding catheter;
   a receptacle of a substantially constant diameter extending logitudinally through the guiding catheter, comprising an elongate tubular shaft having a lumen extending longitudinally therethrough from a proximal end to a distal end;
   a balloon angioplasty catheter extending through said lumen, said angioplasty catheter and said receptacle each adapted to slide longitudinally with respect to each other; and
   a longitudinally movable guidewire extending through said lumen, wherein said guidewire is outside of said angioplasty catheter along the entire length of the catheter.

6. The system of claim 5, wherein said angioplasty catheter is a peripheral angioplasty catheter.

7. The system of claim 5, wherein said angioplasty catheter is a fixed wire coronary balloon angioplasty catheter.

8. The system of claim 5, wherein the diameter of said receptacle shaft is 3.9 French or smaller.

9. The system of claim 8, wherein said receptacle further comprises an enlarged connector at the proximal end thereof through which said angioplasty catheter extends into said lumen.

10. The system of claim 5, wherein said receptacle includes a side port extending through said shaft and adapted to receive a guidewire extending therethrough.

11. The system of claim 10, wherein said side port is located toward the proximal end of said receptacle at a point ordinarily outside a patient during use of said system.

12. The system of claim 5, wherein said receptacle further includes a guidewire removing means for permitting removal of the guidewire laterally through said shaft, said guidewire removing means extending longitudinally along at least a portion of said shaft.

13. The system of claim 12, wherein said guidewire removing means comprises a slit.

14. The system of claim 12, wherein said guidewire removing means is adapted to form a slit when lateral removal of said guidewire is desired.

15. The system of claim 12, wherein said guidewire removing means extends distally along said shaft to within about 40 cm of the distal end of said receptacle.

16. The system of claim 12, wherein said guidewire removing means extends distally along said shaft to the distal end of said receptacle.

17. The system of claim 12, wherein said shaft further includes a side port adapted to receive a guidewire extending therethrough into said lumen, said side port located at a point ordinarily outside the body during use, and wherein said guidewire removing means extends distally from said side port.

18. The system of claim 5, wherein said shaft has a first proximal segment and a second distal segment, and wherein said first segment is more rigid than said second segment.

19. The system of claim 18, wherein said first segment is made of a different material than said second segment.

20. The system of claim 18, wherein said second segment is between about 1 and about 20 cm in length.

21. A bailout system for procedures involving balloon angioplasty catheters, comprising:
a receptacle comprising an elongate tubular shaft having a lumen of a substantially constant diameter extending longitudinally therethrough from a proximal end to a distal end, said receptacle being adapted to extend longitudinally through a guiding catheter, and a side port extending through said shaft adapted to receive a guidewire extending therethrough;
a balloon angioplasty catheter extending through said lumen, said angioplasty catheter and said receptacle each adapted to freely slide longitudinally with respect to each other, wherein the balloon angioplasty catheter has an angioplasty balloon having a maximum inflated diameter, and wherein the diameter of the lumen in the receptacle is not greater than the maximum inflated diameter of the balloon; and
a longitudinally movable guidewire extending through said lumen, wherein said guidewire is outside of said catheter along the entire length of said catheter.

22. The system of claim 21, wherein said side port is located toward the proximal end of said receptacle at a point ordinarily outside a patient during use of said system.

23. The system of claim 21, wherein said receptacle further includes a guidewire removing means for permitting removal of the guidewire laterally through said shaft, said guidewire removing means extending longitudinally along at least a portion of said shaft.

24. The system of claim 23, wherein said guidewire removing means comprises a slit.

25. The system of claim 23, wherein said guidewire removing means is adapted to form a slit when lateral removal of said guidewire is desired.

26. The system of claim 23, wherein said guidewire removing means extends distally along said shaft to within about 40 cm of the distal end of said receptacle.

27. The system of claim 23, wherein said guidewire removing means extends distally along said shaft to the distal end of said receptacle.

28. The system of claim 23, wherein said shaft further includes a proximal side port adapted to receive a guidewire extending therethrough into said lumen, and wherein said guidewire removing means extends distally from said side port.

29. The system of claim 21, wherein said shaft has a first proximal segment and a second distal segment, and wherein said first segment is more rigid than said second segment.

30. The system of claim 29, wherein said first segment is made of a different material than said second segment.

31. The system of claim 29, wherein said second segment is between about 1 and about 20 cm in length.

* * * * *